United States Patent [19]

Uchida et al.

[11] Patent Number: 5,180,519

[45] Date of Patent: Jan. 19, 1993

[54] ALKENYL ETHER DERIVATIVE AND LIQUID CRYSTAL COMPOSITION CONTAINING THE SAME

[75] Inventors: Manabu Uchida; Makoto Ushioda; Yasuyuki Goto, all of Chiba, Japan

[73] Assignee: Chisso Corporation, Ohsaka, Japan

[21] Appl. No.: 680,042

[22] Filed: Mar. 29, 1991

Related U.S. Application Data

[63] Continuation of Ser. No. 492,571, Mar. 13, 1990, abandoned.

[30] Foreign Application Priority Data

Mar. 13, 1989 [JP] Japan ................. 1-60411

[51] Int. Cl.$^5$ .............. C09K 19/52; C09K 19/30; C07C 41/00
[52] U.S. Cl. .............. 252/299.63; 252/299.01; 568/579
[58] Field of Search ............. 252/299.01, 299.62, 252/299.63; 350/350 S; 568/579, 664

[56] References Cited

U.S. PATENT DOCUMENTS

| | | | |
|---|---|---|---|
| 4,331,552 | 5/1982 | Eidenschink et al. | 252/299.6 |
| 4,522,741 | 6/1985 | Inoue et al. | 252/299.63 |
| 4,617,141 | 10/1986 | Inoue et al. | 252/299.63 |
| 4,846,998 | 7/1989 | Pohl et al. | 252/299.63 |
| 4,873,019 | 10/1989 | Krause et al. | 252/299.61 |
| 4,913,837 | 4/1990 | Gray et al. | 252/299.61 |
| 5,102,578 | 4/1992 | Buchecker et al. | 252/299.63 |

FOREIGN PATENT DOCUMENTS 0355552  2/1990  European Pat. Off. .

OTHER PUBLICATIONS

Chemical Abstract CA 100(20): 157255h.

*Primary Examiner*—Robert L. Stoll
*Assistant Examiner*—Shean C. Wu
*Attorney, Agent, or Firm*—Wenderoth, Lind & Ponack

[57] ABSTRACT

An alkenyl ether derivative having a low viscosity, a good compatibility with other liquid crystalline compounds and being capable of use in preparing a liquid crystal display element having a high response rate are provided, which derivative is expressed by the formula $$R_1-CH_2-O-(CH_2)_n-A_1-A_2A_3-R_2 \quad [1]$$

wherein $R_1$ is a 2-7C alkenyl group having a double bond at its terminal or a double bond of a trans configuration at a position other than its terminal, $R_2$ is 1-10C alkyl group or alkoxy group, $A_1$ and $A_2$ each independently are a 1,4-phenylene or a trans-1,4-cyclohexylene, $A_3$ represents a 1,4-phenylene, a trans-1,4-cyclohexylene or a single bond and n is 1 or 2.

5 Claims, No Drawings

ALKENYL ETHER DERIVATIVE AND LIQUID CRYSTAL COMPOSITION CONTAINING THE SAME

This application is a continuation of now abandoned application, Ser. No. 07/492,571 filed Mar. 13, 1990.

BACKGROUND OF THE INVENTION

1. Field of the Invention

This invention relates to an alkenyl ether derivative and liquid crystal composition containing the same. More particularly it relates to an alkenyl ether derivative capable of use in preparing a liquid crystal display element having a high response rate.

2. Description of the Related Art

In recent years, liquid crystals have been growing in importance from the aspect of dielectrics of display elements due to their electrooptical effect based upon the dielectric anisotropy and the optical anisotropy thereof. Display modes based upon liquid crystals include for example, dynamic scattering mode, phase transition mode, DAP mode, guest-host mode, TN mode using a 90° twist cell, STN or SBE mode using a 180° to 270° twist cell, etc. Liquid crystal materials used for these display modes are required to exhibit various characteristics such as broad mesomorphic range, stability to environmental factors, e.g. moisture, heat, air, light, electricity, etc., colorlessness, rapid response time, etc.

Since the response time has a relation proportional to the viscosity of the liquid crystal materials, use of a liquid crystal material having a low viscosity makes it possible to raise the response rate.

At present, however, there is no single compound capable of sufficiently driving display elements; hence, practically, liquid crystal mixtures obtained by blending several kinds of liquid crystalline compounds, that is, liquid crystal compounds or compounds potentially having liquid crystallinity, have been used. Thus, the liquid crystalline compounds are also required to have a good compatibiltiy with other liquid crystal compounds.

SUMMARY OF THE INVENTION

The object of the present invention is to provide an alkenyl ether compound having a low viscosity and a good compatibility with other liquid crystalline compounds and capable of use in preparing a liquid crystal display element having a high response rate, among the above-mentioned various characteristics of liquid crystal materials.

The present invention resides in an alkenyl ether compound expressed by the formula $$R_1-CH_2-O-(CH_2)_n-A_1-A_2-A_3-R_2 \quad [I]$$

wherein $R_1$ represents an alkenyl group of 2 to 7 carbon atoms having a double bond at its terminal (the terminal after $R_1$ is bound to the adjacent $CH_2$) or a double bond of a trans configuration at a position other than its terminal, $R_2$ represents an alkyl group or an alkoxy group each of 1 to 10 carbon atoms, $A_1$ and $A_2$ each independently represent a 1,4-phenylene or a trans-1,4-cyclohexylene, $A_3$ represents a 1,4-phenylene, a trans-1,4-cyclohexylene or a single bond and n represents 1 or 2.

DETAILED DESCRIPTION OF PREFERRED EMBODIMENTS

The compound of the formula (I) of the present invention can be prepared according to the following process:

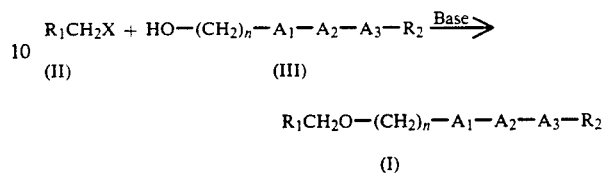

wherein $R_1$, $R_2$, $A_1$, $A_2$, $A_3$ and n are as defined above, and X represents F, Cl, Br, I or another eliminating group, preferably a tosyloxy group or mesyloxy group.

Namely, a base such as sodium hydride, sodium, potassium hydride, etc. is reacted with the compound [III] in an aprotic organic solvent such as THF, DMF, DMSO, etc., followed by adding the compound [II] to obtain the compound of the formula [I] of the present invention.

Since the thus obtained compound of the formula [I] of the present invention is stable to environmental factors such as moisture, heat, air, light, electricity, etc. and colorlessness and has a low viscosity, it is possible to have a rapid response rate of liquid crystal display elements, and further since the compound exhibits a superior compatibility with other existing liquid crystalline compounds such as ester compounds, Schiff's compounds, ethane compounds, acetylene compounds, azoxy compounds, biphenyl compounds, cyclohexane compounds, cyclohexene compounds, pyridine compounds, pyrimidine compounds, dioxane compounds, etc., admixture of the compound with these compounds or mixtures thereof can afford liquid crystal materials suitable for various applications.

Particularly preferred examples of the compound of the formula [I] are as follows. $R_1$, $R_2$ and n in these examples are as defined above:

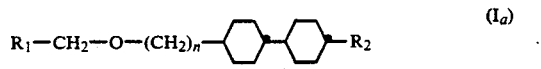

(I$_a$)

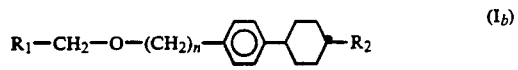

(I$_b$)

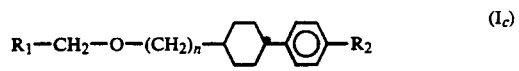

(I$_c$)

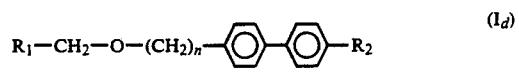

(I$_d$)

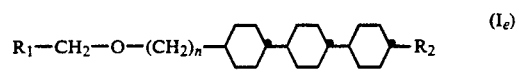

(I$_e$)

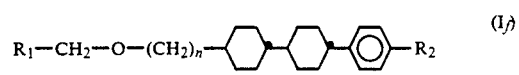

(I$_f$)

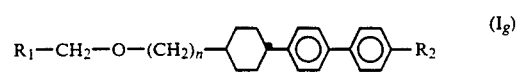

(I$_g$)

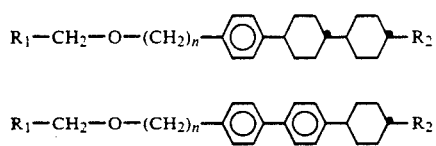

(I$_h$)

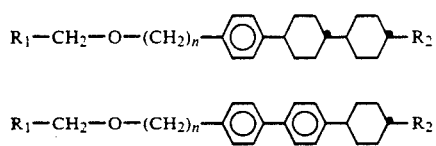

(I$_i$)

Among the above examples, compounds wherein R$_1$ is CH$_2$=CH— or (E)—CH$_3$CH=CH— and R$_2$ has 1 to 5 carbon atoms are preferable. The compound of the formula [Ia] is most preferable.

The liquid crystal composition of the present invention comprises at least two liquid crystals or liquid crystalline compounds at least one of which is a liquid crystalline compound expressed by the above formula [I].

As compounds used in admixture with the compound of the formula [I] as a component of the liquid crystal composition of the present invention, known compounds expressed by the following formulas (i) to (xxxiii) are exemplified:

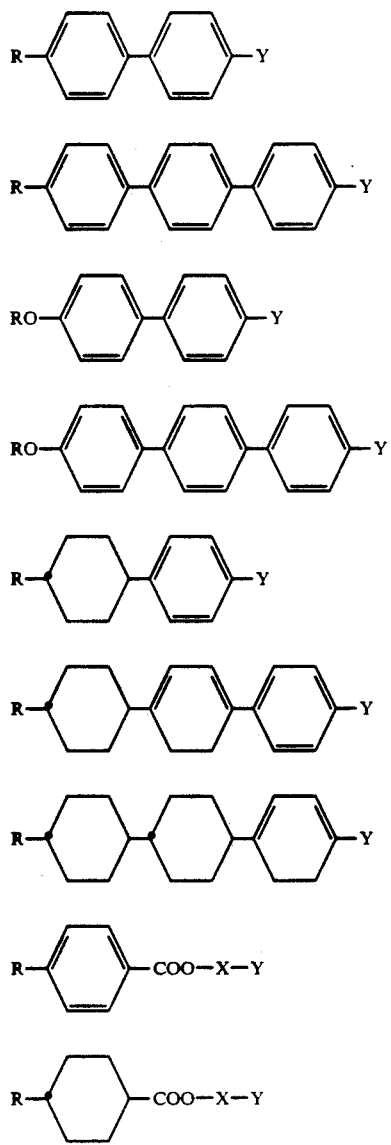

(i)

(ii)

(iii)

(iv)

(v)

(vi)

(vii)

(viii)

(ix)

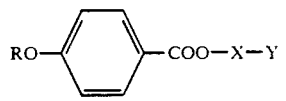 (x)

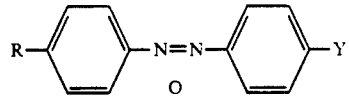 (xi)

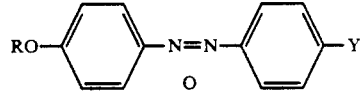 (xii)

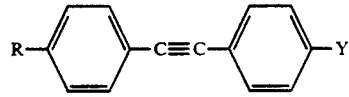 (xiii)

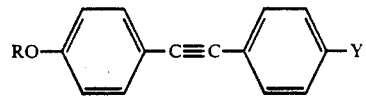 (xiv)

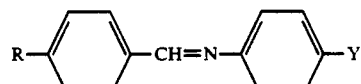 (xv)

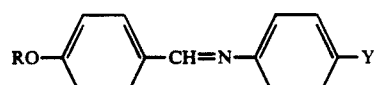 (xvi)

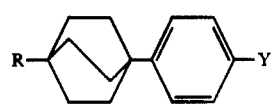 (xvii)

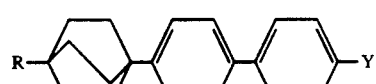 (xviii)

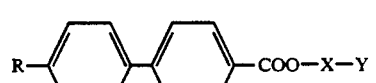 (xix)

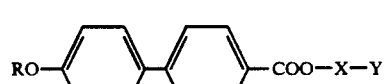 (xx)

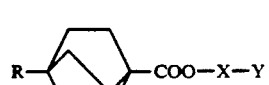 (xxi)

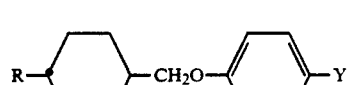 (xxii)

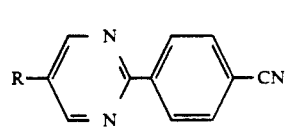 (xxiii)

-continued (xxiv) 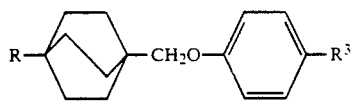

(xxv) 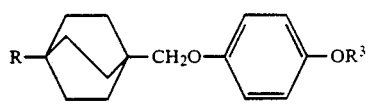

(xxvi) 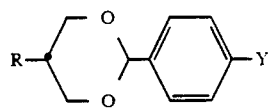

(xxvii) 

(xxviii) 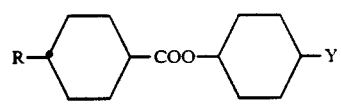

(xxix) 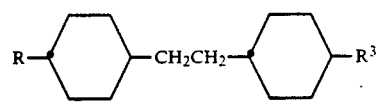

(xxx) 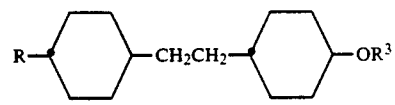

(xxxi) 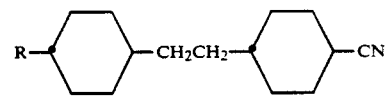

(xxxii) 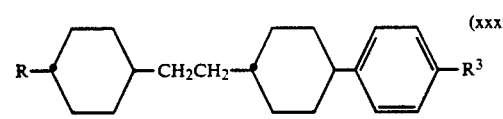

(xxxiii) 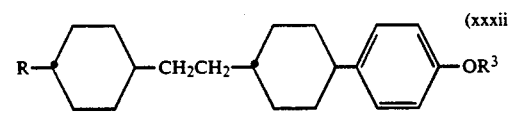

In these formulas (i)-(xxxiii), X represents

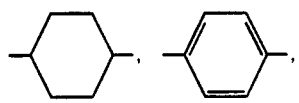

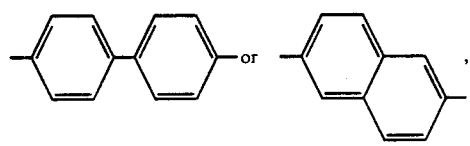

Y represents —CN, halogen atom, $R^3$ or —$OR^3$ and R and $R^3$ each represent an alkyl group or an alkenyl group each of 1 to 10 carbon atoms.

The present invention will be described in more detail by way of Examples, but it should not be construed to be limited thereto. In these Examples, Tm represents melting point and Tc represents a clearing point.

EXAMPLE 1

Preparation of trans-4-allyloxymethyl-(trans-4-n-butylcyclohexyl)cyclohexane (Compound No. 1) (a compound of the formula [I] wherein $R_1$ represents $CH_2=CH-$, $R_2$ represents n—$C_4H_9$—, $A_1$ and $A_2$ both represent

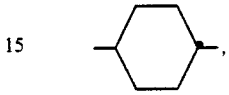

$A_3$ represents a single bond and n represents 1)

(i) Preparation of trans-4-(trans-4-n-butylcyclohexyl)-cyclohexanecarboxyaldehyde Into a three-necked flask having a 200 ml capacity was added a solution of trans-4-(trans-4-n-butylcyclohexyl)cyclohexanecarbonitrile (20.0 g, 0.08 mol) in toluene (50 ml), and cooled to 0° C. To the cooled mixture was dropwise added a solution of diisobutylaluminum hydride (12.6 g, 0.09 mol) in toluene (50 ml), followed by agitating the mixture at room temperature for 3 hours, again cooling the resulting material to 0° C., adding methanol, saturated NH₄Cl aqueous solution and cold dilute sulfuric acid, removing the resulting aqueous layer, washing with saturated sodium hydrogen carbonate aqueous solution, washing with water till the washing water became neutral, drying over anhydrous magnesium sulfate, removing a drying agent, concentrating under reduced pressure, and further distilling under reduced pressure to obtain the captioned compound (14.6 g) having a b.p. of 153° C./3 mmHg.

(ii) Preparation of trans-4-(trans-4-n-butylcyclohexyl)hydroxymethylcyclohexane

Into a three-necked flask having a 300 ml capacity were added sodium borohydride (1.8 g, 0.05 mol) and isopropyl alcohol (30 ml), and cooled to 0° C. To the cooled mixture was dropwise added a solution of the compound obtained in (i) (11.7 g, 0.05 mol) in isopropyl alcohol (50 ml), followed by agitating the mixture at room temperature for 7 hours, again cooling the resulting material to 0° C., adding ethyl acetate and cold dilute hydrochloric acid, removing the resulting aqueous layer, washing the resulting organic layer with 1N NaOH aqueous solution, washing with water till the washing water became neutral, drying over anhydrous sodium sulfate, removing the drying agent, concentrating under reduced pressure, recrystallizing from alcohol and drying to obtain the captioned compound (10.0 g).

(iii) Preparation of trans-4-allyloxymethyl-(trans-4-n-butylcyclohexyl)cyclohexane Into a three-necked flask having a 200 ml capacity were added sodium hydride (0.6 g, 0.03 mol), the compound obtained in (ii) (5.6 g, 0.02 mol) and tetrahydrofuran (40 ml), and agitated for one hour to obtain a resulting mixture. To the mixture was then added a solution of allyl bromide (26.8 g, 0.22 mol) in tetrahydrofuran (50 ml), and refluxed for 20 hours, followed by cooling the resulting material, adding water (50 ml) and heptane (50 ml), removing the resulting aqueous layer, washing the resulting organic layer three times with water (50 ml), drying over anhydrous magnesium sulfate, removing a drying agent, concentrating under reduced pressure, passing the resulting concentrate through an alumina column using heptane solvent, distilling off heptane, recrystallizing from alcohol and drying to obtain the captioned compound (5.9 g). Its structure was confirmed by NMR spectra. Its Tm was −1.0° C. and its Tc was 73° C.

The following compounds were obtained in the same manner as in Example 1:

trans-4-allyloxymethyl-(trans-4-methylcyclohexyl)cyclohexane (Compound No. 2)

trans-4-allyloxymethyl-(trans-4-ethylcyclohexyl)cyclohexane (Compound No. 3)

trans-4-allyloxymethyl-(trans-4-n-propylcyclohexyl)cyclohexane (Compound No. 4), Tc=55° C.

trans-4-allyloxymethyl-(trans-4-n-pentylcyclohexyl)cyclohexane (Compound No. 5), Tc=77° C.

trans-4-allyloxymethyl-(trans-4-n-hexylcyclohexyl)cyclohexane (Compound No. 6)

trans-4-allyloxymethyl-(trans-4-n-heptylcyclohexyl)cyclohexane (Compound No. 7)

trans-4-allyloxymethyl-(trans-4-n-octylcyclohexyl)cyclohexane (Compound No. 8)

trans-4-allyloxymethyl-(trans-4-n-nonylcyclohexyl)cyclohexane (Compound No. 9)

trans-4-allyloxymethyl-(trans-4-n-decylcyclohexyl)cyclohexane (Compound No. 10).

EXAMPLE 2

Preparation of trans-4-allyloxyethyl-(trans-4-n-propylcyclohexyl)cyclohexane (Compound No. 11) (a compound of the formula [I] wherein $R_1$ represents $CH_2=CH-$, $R_2$ represents $n-C_3H_7-$, $A_1$ and $A_2$ both represent

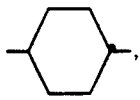

$A_3$ represents a single bond and n represents 2)

(i) Preparation of trans-4-hydroxyethyl-(trans-4-n-propylcyclohexyl)cyclohexane

Into a three-necked flask having a 500 ml capacity was added lithium aluminum hydride (2.8 g), and cooled down to 0° C., followed by dropwise adding tetrahydrofuran (50 ml) and a solution of trans-4-(trans-4-n-propylcyclohexyl)cyclohexyl-acetic acid (26.6 g, 0.1 mol) in this order, agitating the mixture at room temperature for 4 hours to obtain a mixture. To this mixture ethyl acetate (10 ml), water (10 ml) and 2N NaOH aqueous solution (10 ml) were added in this order and refluxed for 30 minutes, followed by cooling the resulting material, filtering, concentrating the filtrate under reduced pressure, adding water (100 ml) and toluene (100 ml), removing the resulting aqueous layer, washing the resulting organic layer with water till the washing water became neutral, drying over anhydrous sodium sulfate, removing a drying agent, concentrating under reduced pressure, passing the residue through an alumina column using dichloromethane solvent, distilling off dichloromethane, recrystallizing from heptane and drying to obtain the captioned compound (21.5 g). Its structure was confirmed by NMR spectra.

(ii) Preparation of trans-4-allyloxyethyl-(trans-4-n-propylcyclohexyl)cyclohexane This compound was obtained in the same manner as in Example 1, (iii). Tc was 32° C.

The following compounds were obtained in the same manner as in Example 2.

trans-4-allyloxyethyl-(trans-4-methylcyclohexyl)cyclohexane (Compound No. 12)

trans-4-allyloxyethyl-(trans-4-ethylcyclohexyl)cyclohexane (Compound No. 13)

trans-4-allyloxyethyl-(trans-4-n-butylcyclohexyl)cyclohexane (Compound No. 14)

trans-4-allyloxyethyl-(trans-4-n-pentylcyclohexyl)cyclohexane (Compound No. 15)

trans-4-allyloxyethyl-(trans-4-n-hexylcyclohexyl)cyclohexane (Compound No. 16)

trans-4-allyloxyethyl-(trans-4-n-heptylcyclohexyl)cyclohexane (Compound No. 17)

trans-4-allyloxyethyl-(trans-4-n-octylcyclohexyl)cyclohexane (Compound No. 18)

trans-4-allyloxyethyl-(trans-4-n-nonylcyclohexyl)cyclohexane (Compound No. 19)

trans-4-allyloxyethyl-(trans-4-n-decylcyclohexyl)cyclohexane (Compound No. 20).

EXAMPLE 3

Preparation of 4-(trans-4'-allyloxymethylcyclohexyl)toluene (Compound No. 21) (a compound of the formula [I] wherein $R_1$ represents $CH_2=CH-$, $R_2$ represents $CH_3-$, $A_1$ represents

$A_2$ represents

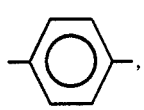

$A_3$ represents a single bond and n represents 1)

Example 2 was repeated except that trans-4-(trans-4-n-propylcyclohexyl)cyclohexyl-acetic acid used in item (i), Example 2 was replaced by trans-4-(4-methylphenyl)cyclohexanecarboxylic acid to obtain the captioned compound.

The following compounds were obtained in the same manner as in Example 3:

4-(trans-4'-allyloxymethyl)cyclohexyl-ethylbenzene (Compound No. 22)

4-(trans-4'-allyloxymethyl)cyclohexyl-n-propylbenzene (Compound No. 23), Tm<20° C.

4-(trans-4'-allyloxymethyl)cyclohexyl-n-butylbenzene (Compound No. 24), Tm=−6° C.

4-(trans-4'-allyloxymethyl)cyclohexyl-n-pentylbenzene (Compound No. 25)

4-(trans-4'-allyloxymethyl)cyclohexyl-n-hexylbenzene (Compound No. 26)

4-(trans-4'-allyloxymethyl)cyclohexyl-n-heptylbenzene (Compound No. 27)

4-(trans-4'-allyloxymethyl)cyclohexyl-n-octylbenzene (Compound No. 28)

4-(trans-4'-allyloxymethyl)cyclohexyl-n-nonylbenzene (Compound No. 29)

4-(trans-4'-allyloxymethyl)cyclohexyl-n-decylbenzene (Compound No. 30).

EXAMPLE 4

Preparation of 4-allyloxymethyl-(trans-4'-n-propylcyclohexyl)benzene (Compound No. 31) (a compound of the formula [I] wherein $R_1$ represents $CH_2=CH-$, $R_2$ represents $n-C_3H_7-$, $A_1$ represents

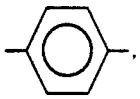

$A_2$ represents

$A_3$ represents a single bond and n represents 1)

(i) Preparation of 4-(trans-4'-n-propylcyclohexyl)benzylalcohol

Into a three-necked flask having a 1 l capacity was added lithium aluminum hydride (5.7 g, 0.15 mol), and cooled down to 0° C., followed by dropwise adding tetrahydrofuran (100 ml) and a solution of 4-(trans-4'-n-propylcyclohexyl)benzoyl chloride (53.0 g, 0.2 mol) in tetrahydrofuran (100 ml) in this order, agitating the mixture at room temperature for 3 hours, again cooling it down to 0° C., adding ethyl acetate (10 ml), water (10 ml) and 2N NaOH aqueous solution (10 ml) in this order, heating the mixture under reflux for 30 minutes, cooling the resulting material, filtering, adding saturated NaCl aqueous solution (100 ml) and ethyl acetate (100 ml), removing the aqueous layer, washing the resulting organic layer with water till the washing water became neutral, drying over anhydrous sodium sulfate, removing a drying agent, concentrating under reduced pressure, recrystallizing from heptane solvent and drying to obtain the captioned compound (35.8 g). Its structure was confirmed by NMR spectra.

(ii) Preparation of 4-allyloxymethyl-(trans-4'-n-propylcyclohexyl)benzene

This compound was obtained in the same manner as in Item (iii), Example 1 (Tm = -25° C.).

The following compounds were obtained in the same manner as in Example 4:

4-allyloxymethyl-(trans-4'-methylcyclohexyl)benzene (Compound No. 32)

4-allyloxymethyl-(trans-4'-ethylcyclohexyl)benzene (Compound No. 33), Tm<20° C.

4-allyloxymethyl-(trans-4'-n-butylcyclohexyl)benzene (Compound No. 34)

4-allyloxymethyl-(trans-4'-n-pentylcyclohexyl)benzene (Compound No. 35)

4-allyloxymethyl-(trans-4'-n-hexylcyclohexyl)benzene (Compound No. 36)

4-allyloxymethyl-(trans-4'-n-heptylcyclohexyl)benzene (Compound No. 37)

4-allyloxymethyl-(trans-4'-n-octylcyclohexyl)benzene (Compound No. 38)

4-allyloxymethyl-(trans-4'-n-nonylcyclohexyl)benzene (Compound No. 39)

4-allyloxymethyl-(trans-4'-n-decylcyclohexyl)benzene (Compound No. 40).

EXAMPLE 5

Preparation of 4-allyloxymethyl-4'-n-propoxybiphenyl (Compound No. 41) (a compound of the formula [I] wherein $R_1$ represents $CH_2=CH-$, $R_2$ represents $n-C_3H_7O-$, $A_1$ and $A_2$ both represent

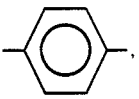

$A_3$ represents a single bond and n represents 1)

(i) Preparation of ethyl-4-(4-n-propoxyphenyl) benzoate

Into a three-necked flask having a 500 ml capacity were added ethyl-4-(4-hydroxyphenyl) benzoate (17.0 g, 0.07 mol), n-propyl bromide (12.9 g, 0.11 mol), KOH (4.8 g, 0.08 mol) and ethanol (250 ml), followed by heating the mixture under reflux for 4 hours, cooling the resulting material, adding water (500 ml) and ethyl acetate (500 ml), washing the resulting organic layer with water till the washing water became neutral, drying over anhydrous sodium sulfate, removing a drying agent, concentrating under reduced pressure, passing the concentrate through a silica gel column using dichloromethane solvent, recrystallizing from n-heptane solvent and drying to obtain the captioned compound (16.0 g, Tm=131.6° C.).

(ii) Preparation of 4-allyloxymethyl-4'-n-propoxybiphenyl

This compound was obtained in the same manner as in Example 5 (Tm=80° C.).

The following compounds were obtained in the same manner as in Example 5:

4-allyloxymethyl-4'-methoxybiphenyl (Compound No. 42)

4-allyloxymethyl-4'-ethoxybiphenyl (Compound No. 43)

4-allyloxymethyl-4'-n-butoxybiphenyl (Compound No. 44) Tm=82° C.

4-allyloxymethyl-4'-n-pentyloxybiphenyl (Compound No. 45)

4-allyloxymethyl-4'-n-hexyloxybiphenyl (Compound No. 46)

4-allyloxymethyl-4'-n-heptyloxybiphenyl (Compound No. 47)

4-allyloxymethyl-4'-n-octyloxybiphenyl (Compound No. 48)

4-allyloxymethyl-4'-n-nonyloxybiphenyl (Compound No. 49)

4-allyloxymethyl-4'-n-decyloxybiphenyl (Compound No. 50).

EXAMPLE 6

Preparation of 4'-(trans-4''-allyloxymethylcyclohexyl)4-n-propylbiphenyl (Compound No. 51) (a compound of the formula [I] wherein $R_1$ represents $CH_2=CH-$, $R_2$ represents $n-C_3H_7-$, $A_1$ represents

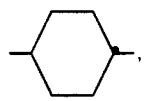

$A_2$ and $A_3$ both represent

and n represents 1)

(i) Preparation of 4'-(trans-4"-hydroxymethylcyclohexyl)-4-n-propylbiphenyl

Into a three-necked flask having 300 ml capacity was added lithium aluminum hydride (0.8 g, 0.02 mol), and cooled down to 0° C., followed by dropwise adding tetrahydrofuran (20 ml) and a solution of 4'-(trans-4"-carboxycyclohexyl)-4-n-propylbiphenyl (8.2 g, 0.025 mol) in tetrahydrofuran (100 ml) in this order, heating the mixture under reflux for 6 hours, cooling the resulting material down to 0° C., adding ethyl acetate (10 ml) and 6N hydrochloric acid (50 ml), vigorously agitating the mixture, extracting with ethyl acetate, washing the resulting organic layer with 2N NaOH aqueous solution (100 ml), further washing it with water till the washing water became neutral, drying over anhydrous sodium sulfate, removing the drying agent, concentrating under reduced pressure, passing the concentrate through an alumina column using dichloromethane solvent, recrystallizing from alcohol and drying the captioned compound (5.3 g).

(ii) Preparation of 4'-(trans-4"-allyloxymethylcyclohexyl)-4-n-propylbiphenyl

This compound was obtained in the same manner as in Example 1, (iii). Tc=137° C.

The following compounds were obtained in the same manner as in Example 6:

4'-(trans-4"-allyloxymethylcyclohexyl)-4-methylbiphenyl (Compound No. 52)

4'-(trans-4"-allyloxymethylcyclohexyl)-4-ethylbiphenyl (Compound No. 53)

4'-(trans-4"-allyloxymethylcyclohexyl)-4-n-butylbiphenyl (Compound No. 54)

4'-(trans-4"-allyloxymethylcyclohexyl)-4-n-pentylbiphenyl (Compound No. 55)

4'-(trans-4"-allyloxymethylcyclohexyl)-4-n-hexylbiphenyl (Compound No. 56)

4'-(trans-4"-allyloxymethylcyclohexyl)-4-n-heptylbiphenyl (Compound No. 57)

4'-(trans-4"-allyloxymethylcyclohexyl)-4-n-octylbiphenyl (Compound No. 58)

4'-(trans-4"-allyloxymethylcyclohexyl)-4-n-nonylbiphenyl (Compound No. 59)

4'-(trans-4"-allyloxymethylcyclohexyl)-4-n-decylbiphenyl (Compound No. 60).

EXAMPLE 7

Preparation of trans-4-(trans,trans-4-n-propyl-4"-bicyclohexyl)allyloxymethylcyclohexane (Compound No. 61) (a compound of the formula [I] wherein $R_1$ represents $CH_2=CH-$, $R_2$ represents $n-C_3H_7-$, $A_1$, $A_2$ and $A_3$ all represent

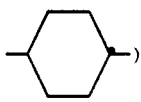

Example 1 was repeated except that trans-4-(trans-4-n-butylcyclohexyl)cyclohexanecarbonitrile was replaced by trans-4-(trans-4-n-propylbicyclohexyl)cyclohexanecarbonitrile to obtain the captioned compound.

The following compounds were obtained in the same manner as in Example 7:

trans-4-(trans,trans-4-methyl-4'-bicyclohexyl)allyloxymethylcyclohexane (Compound No. 62)

trans-4-(trans,trans-4-ethyl-4'-bicyclohexyl)allyloxymethylcyclohexane (Compound No. 63)

trans-4-(trans,trans-4-n-butyl-4'-bicyclohexyl)allyloxymethylcyclohexane (Compound No. 64)

trans-4-(trans,trans-4-n-pentyl-4'-bicyclohexyl)allyloxymethylcyclohexane (Compound No. 65)

trans-4-(trans,trans-4-n-hexyl-4'-bicyclohexyl)allyloxymethylcyclohexane (Compound No. 66)

trans-4-(trans,trans-4-n-heptyl-4'-bicyclohexyl)allyloxymethylcyclohexane (Compound No. 67)

trans-4-(trans,trans-4-n-octyl-4'-bicyclohexyl)allyloxymethylcyclohexane (Compound No. 68)

trans-4-(trans,trans-4-n-nonyl-4'-bicyclohexyl)allyloxymethylcyclohexane (Compound No. 69)

trans-4-(trans,trans-4-n-decyl-4'-bicyclohexyl)allyloxymethylcyclohexane (Compound No. 70)

EXAMPLE 8

Preparation of 4-(trans,trans-4-n-propyl-4'-bicyclohexyl)allyloxymethylbenzene (Compound No. 71) (a compound of the formula [I] wherein $R_1$ represents $CH_2=CH-$, $R_2$ represents $n-C_3H_7-$, $A_1$ represents

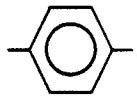

$A_2$ and $A_3$ both represent

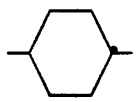

and n represents 1)

Example 1 was repeated except that trans-4-(trans-4-n-butylcyclohexyl)cyclohexanecarbonitrile in Example 1 was replaced by 4-(trans,trans-4-n-propyl-4'-bicyclohexyl)benzonitrile to obtain the captioned compound.

The following compounds were obtained in the same manner as in Example 8:

4-(trans,trans-4-methyl-4'-bicyclohexyl)allyloxymethylbenzene (Compound No. 72)

4-(trans,trans-4-ethyl-4'-bicyclohexyl)allyloxymethylbenzene (Compound No. 73)

4-(trans,trans-4-n-butyl-4'-bicyclohexyl)allyloxymethylbenzene (Compound No. 74)

4-(trans,trans-4-n-pentyl-4'-bicyclohexyl)allyloxymethylbenzene (Compound No. 75)

4-(trans,trans-4-n-hexyl-4'-bicyclohexyl)allyloxymethylbenzene (Compound No. 76)

4-(trans,trans-4-n-heptyl-4'-bicyclohexyl)allyloxymethylbenzene (Compound No. 77)

4-(trans,trans-4-n-octyl-4'-bicyclohexyl)allyloxymethylbenzene (Compound No. 78)

4-(trans,trans-4-n-nonyl-4'-bicyclohexyl)allyloxymethylbenzene (Compound No. 79)

4-(trans,trans-4-n-decyl-4'-bicyclohexyl)allyloxymethylbenzene (Compound No. 80).

EXAMPLE 9

Preparation of 4-allyloxymethyl-4'-(trans-4-n-propylcyclohexyl)biphenyl (Compound No. 81) (a compound of the formula [I] wherein $R_1$ represents $CH_2=CH-$, $R_2$ represents $n-C_3H_7-$, $A_1$ and $A_2$ both represent

$A_3$ represents

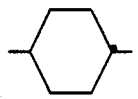

and n represents

Example 1 was repeated except that trans-4-(trans-4-n-butylcyclohexyl)cyclohexanecarbonitrile in Example 1 was replaced by 4-(trans-4-n-propylcyclohexyl)-4'-cyanobiphenyl to obtain the captioned compound.

The following compounds were obtained in the same manner as in Example 9:

4-allyloxymethyl-4'-(trans-4-methylcyclohexyl)biphenyl (Compound No. 82)
4-allyloxymethyl-4'-(trans-4-ethylcyclohexyl)biphenyl (Compound No. 83)
4-allyloxymethyl-4'-(trans-4-n-butylcyclohexyl)biphenyl (Compound No. 84)
4-allyloxymethyl-4'-(trans-4-n-pentylcyclohexyl)biphenyl (Compound No. 85)
4-allyloxymethyl-4'-(trans-4-n-hexylcyclohexyl)biphenyl (Compound No. 86)
4-allyloxymethyl-4'-(trans-4-n-heptylcyclohexyl)biphenyl (Compound No. 87)
4-allyloxymethyl-4'-(trans-4-n-octylcyclohexyl)biphenyl (Compound No. 88)
4-allyloxymethyl-4'-(trans-4-n-nonylcyclohexyl)biphenyl (Compound No. 89)
4-allyloxymethyl-4'-(trans-4-n-decylcyclohexyl)biphenyl (Compound No. 90)

EXAMPLE 10

Preparation of 4-(trans,trans-4-allyloxymethyl-4'-bicyclohexyl-n-propylbenzene (Compound No. 91) (a compound of the formula [I] wherein $R_1$ represents $CH_2=CH-$, $R_2$ represents $n-C_3H_7-$, $A_1$ and $A_2$ both represent

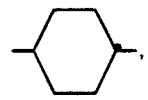

$A_3$ represents

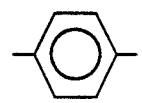

and n represents 1)

Example 1 (iii) was repeated except that trans-4-(trans-4-n-butylcyclohexyl)hydroxymethylcyclohexane in Example 1 (iii) was replaced by 4-(trans,trans-4-hydroxymethyl-4'-bicyclohexyl)-n-propylbenzene to obtain the captioned compound.

The following compounds were prepared in the same manner as in Example 10:

4-(trans,trans-4-allyloxymethyl-4'-bicyclohexyl)toluene (Compound No. 92)
4-(trans,trans-4-allyloxymethyl-4'-bicyclohexyl)ethylbenzene (Compound No. 93)
4-(trans,trans-4-allyloxymethyl-4'-bicyclohexyl)-n-butylbenzene (Compound No. 94)
4-(trans,trans-4-allyloxymethyl-4'-bicyclohexyl)-n-pentylbenzene (Compound No. 95)
4-(trans,trans-4-allyloxymethyl-4'-bicyclohexyl)-n-hexylbenzene (Compound No. 96)
4-(trans,trans-4-allyloxymethyl-4'-bicyclohexyl)-n-heptylbenzene (Compound No. 97)
4-(trans,trans-4-allyloxymethyl-4'-bicyclohexyl)-n-octylbenzene (Compound No. 98)
4-(trans,trans-4-allyloxymethyl-4'-bicyclohexyl)-n-nonylbenzene (Compound No. 99)
4-(trans,trans-4-allyloxymethyl-4'-bicyclohexyl)-n-decylbenzene (Compound No. 100).

EXAMPLE 11

Preparation of trans-4-(E)-crotyloxymethyl-(trans,trans-4-n-propyl-4'-bicyclohexyl)cyclohexane (Compound No. 101) (a compound of the formula [I] wherein $R_1$ represents (E)—$CH_3CH=CH-$, $R_2$ represents $n-C_3H_7-$, $A_1$ and $A_2$ both represent

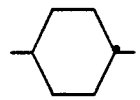

and n represents 1)

Example 7 was repeated except that allyl bromide in Example 7 was replaced by (E)-crotyl chloride to obtain the captioned compound.

The following compounds were obtained in the same manner as in Example 11:

trans-4-(E)-crotyloxymethyl-(trans,trans-4-methyl-4'-bicyclohexyl)cyclohexane (Compound No. 102)
trans-4-(E)-crotyloxymethyl-(trans,trans-4-ethyl-4'-bicyclohexyl)cyclohexane (Compound No. 103)
trans-4-(E)-crotyloxymethyl-(trans,trans-4-n-butyl-4'-bicyclohexyl)cyclohexane (Compound No. 104)
trans-4-(E)-crotyloxymethyl-(trans,trans-4-n-pentyl-4'-bicyclohexyl)cyclohexane (Compound No. 105)
trans-4-(E)-crotyloxymethyl-(trans,trans-4-n-hexyl-4'-bicyclohexyl)cyclohexane (Compound No. 106)
trans-4-(E)-crotyloxymethyl-(trans,trans-4-n-heptyl-4'-bicyclohexyl)cyclohexane (Compound No. 107)
trans-4-(E)-crotyloxymethyl-(trans,trans-4-n-octyl-4'-bicyclohexyl)cyclohexane (Compound No. 108)
trans-4-(E)-crotyloxymethyl-(trans,trans-4-n-nonyl-4'-bicyclohexyl)cyclohexane (Compound No. 109)
trans-4-(E)-crotyloxymethyl-(trans,trans-4-n-decyl-4'-bicyclohexyl)cyclohexane (Compound No. 110).

EXAMPLE 12 (USE EXAMPLE)

To a nematic liquid crystal composition A consisting of

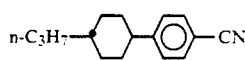 25.5 wt. parts

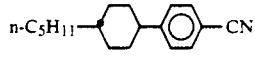 34 wt. parts

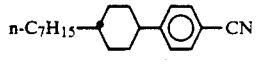 25.5 wt. parts

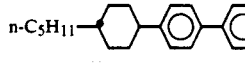 15 wt. parts was added trans-4-allyloxymethyl-(trans-4-n-propylcyclohexyl)cyclohexane (Compound No. 4) as a compound of the present invention shown in Example 4 in a quantity of 15 parts by weight. The viscosity of the resulting composition lowered from 27.0 cp down to 22.5 cP.

Similarly, to the nematic liquid crystal composition A were added each of Compound Nos. 1, 4, 5, 11, 23, 24, 31 and 33 each in an amount of 15 parts by weight as compounds of the present invention to obtain 8 liquid crystal compositions.

The respective viscosities of these compositions are shown in Table 1 together with the above viscosity 22.5 cP in Example 12.

TABLE 1

| Composition No. | Compound No. | Viscosity (cP) |
|---|---|---|
| 1 | 4 | 22.5 |
| 2 | 1 | 23.4 |
| 3 | 5 | 24.0 |
| 4 | 11 | 23.4 |
| 5 | 23 | 20.1 |
| 6 | 24 | 24.2 |
| 7 | 31 | 23.4 |
| 8 | 33 | 22.7 |

TABLE 1-continued

When the compound of the present invention is added to a liquid crystal composition, it is possible to lower the viscosity of the liquid crystal composition, and also it is possible to prepare a liquid crystal display device having a high response rate.

Further, since the compound of the present invention has a good compatibility with other liquid crystalline compounds, it is possible to add the compound in a relatively large quantity, so that it is possible to prepare a liquid crystal composition having a low viscosity.

What we claim is:

1. An alkenyl ether compound expressed by the formula $$R_1-CH_2-O-(CH_2)n-A_1-A_2-A_3-R_2 \qquad [I]$$

wherein $R_1$ represents an alkenyl group of 2 to 7 carbon atoms having a double bond at its terminal or a double bond of a trans configuration at a position other than its terminal, $R_2$ represents an alkyl group or an alkoxy group each of 1 to 10 carbon atoms, $A_1$ and $A_2$ each independently represent a 1,4-phenylene or a trans-1,4-cyclohexylene, $A_3$ represents a 1,4-phenylene, a trans-1,4-cyclohexylene or a single bond and n represents 1 or 2.

2. An alkenyl ether compound according to claim 1, wherein said $R_1$ represents $CH_2=CH-$.

3. An alkenyl ether compound according to claim 1, wherein said $R_1$ represents (E)—$CH_3CH=CH-$.

4. An alkenyl ether compound according to claim 1, wherein said $R_2$ represents an alkyl group or an alkoxy group each of 1 to 5 carbon atoms.

5. A liquid crystal composition comprising at least two components at least one of which is an alkenyl ether compound as set forth in claim 1.

* * * * *